US005698420A

United States Patent [19]

Lam

[11] Patent Number: 5,698,420
[45] Date of Patent: Dec. 16, 1997

[54] PREPARATION OF 4-DEOXY-O-MYCAMINOSYLTYLONOLIDE

[75] Inventor: Lapyuen H. Lam, Redwood City, Calif.

[73] Assignee: Pfizer Inc., New York, N.Y.

[21] Appl. No.: 757,033

[22] Filed: Nov. 26, 1996

Related U.S. Application Data

[60] Provisional application No. 60/007,980 Dec. 5, 1995.

[51] Int. Cl.[6] .......................... C12P 19/60; C12P 19/62; C12N 1/20

[52] U.S. Cl. .......................... 435/76; 435/75; 435/253.5; 435/896; 536/7.1; 514/30

[58] Field of Search .............................. 435/76, 75, 896, 435/253.5; 536/7.1; 514/30

[56] References Cited

FOREIGN PATENT DOCUMENTS 0187049 2/1986 European Pat. Off. .

OTHER PUBLICATIONS

H. Imai et al., J. Antibiotics, 42: pp. 1000–1002, (1989).
A. Tanaka et al., J. Antibiotics, 34: pp. 1374–1376 (1981).

*Primary Examiner*—Herbert J. Lilling
*Attorney, Agent, or Firm*—Peter C. Richardson; Gregg C. Benson; A. Dean Olson

[57] ABSTRACT

Preparation of 4'-deoxy-O-mycaminosyltylonolide by feeding repromicin to a fermentation broth of a strain of the microorganism *Streptomyces fradiae* (ATCC 31733) under aerobic conditions in an aqueous nutrient medium containing inorganic salts and assimilable sources of carbon and nitrogen.

4 Claims, No Drawings

PREPARATION OF 4-DEOXY-O-MYCAMINOSYLTYLONOLIDE

CROSS REFERENCE TO RELATED APPLICATION

This application is a nonprovisional application claiming benefit of provisional application number 60/007,980, filed Dec. 5, 1995.

BACKGROUND OF THE INVENTION

This invention is concerned with a novel process for the preparation of 4'-deoxy-O-mycaminosyltylonolide (4'-deoxy-OMT) comprising feeding repromicin to a fermentation of a strain of the microorganism *Streptomyces fradiae* (ATCC 55671 deposited May 19, 1995) under aerobic conditions in an aqueous nutrient medium containing inorganic salts and assimilable sources of carbon and nitrogen.

4'-Deoxy-O-mycaminosyltylonolide is a chemical compound belonging to the family of macrolide antibiotics. It possesses antibiotic activity, however, its principal use is as an intermediate for more potent antibiotics. Most of the derivatization of 4'-deoxy-O-mycaminosyltylonolide is carried out at the aldehyde functional group in the C-20 position.

SUMMARY OF THE INVENTION

This invention relates to a novel process for preparing an antibacterial macrolide agent. A process is disclosed for preparing 4'-deoxy-O-mycaminosyltylonolide (I) by feeding repromicin (II) to a fermentation broth of a strain of the microorganism *Streptomyces fradiae,* ATCC 31733, under aerobic conditions in an aqueous nutrient medium containing inorganic salts and assimilable sources of carbon and nitrogen. Repromicin may be prepared by a direct fermentation process, as described hereinbelow.

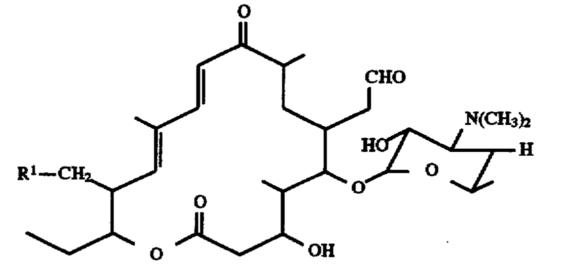

| Formula | Compound Name | $R^1$ |
|---|---|---|
| I | 4'-Deoxy-O-mycaminosyltylonolide | OH |
| II | Repromicin | H |

The utility of the process of the invention is a result of its selectivity and productivity. Compared to direct fermentations reported in the literature (H. Imai et al., EP 187049 A2, (1986); H. Imai et al. (1989), J. Antibiotics 42: 1000–1002), the process of the present invention gives higher concentrations of the desired product and fewer unwanted by-products, making recovery of the desired product easier (A. Tanaka et al., (1981), J. Antibiotics 34: 1374–1376). The process described herein gives improved yields compared to synthetic processes for obtaining the desired product.

DETAILED DESCRIPTION OF THE INVENTION

The starting material repromicin was prepared according to the following fermentation procedure.

Fermentor scale

To prepare frozen lots for use as standard inoculum, *Micromonospora rosaria,* ATCC 55709, deposited Sep. 5, 1995, was inoculated into JDYTT medium (cerelose 10 g/L, corn starch 5 g/L, corn steep solids 2.5 g/L, NZ Amine YTT 5 g/L, $CoCl_2.6H_2O$0.002 g/L, P-2000 (polyglycol, available from George Mann & Co., Inc., 175 Terminal Road, Providence, R.I.) 1 ml/L, $CaCO_3$ 3 g/L) and shaken (250 rpm, 30° C., 2 inch throw) for about three days. The JDYTT medium, adjusted to about pH 7.0, was sterilized at about 121° C. for about 30 minutes prior to use. Glycerol (final concentration 20%) was added as a cryoprotectant, and the culture was stored at about −80° C. To prepare the inoculum, 5 ml of the frozen culture lot was transferred to 1 liter of JDYTT medium in a 2.8 L fernbach flask. The culture was grown for about 3 days at about 30° C. with shaking (250 rpm, 2 inch throw). The entire contents of the fernbach were transferred to 8 L of production medium RSM-6 in a 14 L fermentor jar (New Brunswick Scientific, New Brunswick, N.J.) with two 4¾ inch agitator blades. The composition of RSM-6 was corn starch 50 g/L, cerelose 10 g/L, ardamine PH 5 g/L (available from Champlain Industries Inc., 79 State Street, Harbor Beach, Mich.), Pharmamedia 8–10 g/L (available from The Buckeye Cellulose Corporation, P.O. Box 8407, Memphis, Tenn.), $MgHPO_4.3H_2O$ 10 g/L, casein hydrolysate 2.5 g/L (available from Sheffield Chemical, Norwich, N.Y.), asparagine 0.5 g/L, $FeSO_4.7H_2O$ 0.028 g/L, $MgSO_4.7H_2O$ 0.05 g/L, $K_2HPO_4$ 0.75 g/L, $CuSO_4.5H_2O$ 0.003 g/L, $MnCl_2.4H_2O$ 0.003 g/L, $ZnSO_4.7H_2O$ 0.003 g/L, $CoCl_2.6H_2O$ 0.003 g/L, P2000 1 ml/L. RSM-6 was adjusted to about pH 7.0 and autoclaved for about 99 minutes at about 121° C. prior to use. The fermentation was run at about 30° C., 450 rpm, 0.34 v/v/m air, with pH controlled between 6.7 and 7.3 with $NaOH/H_2SO_4$ or by addition of 6 g/L MOPS to production medium. Repromicin titers typically peaked between 69 and 116 hours. Samples were extracted into a solvent mixture (3.5:6.5 methanol:0.1M $KH_2PO_4$ buffer, pH 3.5). *M. rosaria,* ATCC 55709, produced 368–398 mg/AIL repromicin under these conditions.

Flask scale

Inoculum was prepared as described above or by adding 2 ml of frozen culture lot to 30 ml JDYTT inoculum medium in a 300 ml Erlenmeyer flask. The culture was grown for about 3 days at about 30° C. with shaking (250 rpm, 2 inch throw). Two ml of inoculum were transferred into about 30 ml modified RSM-5 medium (corn starch 30 g/L, 10 g/L pharmamedia, 10 g/L cerelose, 5.0 g/L ardamine PH, 0.5 g/L asparagine, $FeSO_4.7H_2O$ 0.0280 g/L, $MgSO_4.7H_2O$ 0.5 g/L, $K_2HPO_4$ 0.75 g/L, $CUSO_4.5H_2O$ 0.002 g/L, $MnCl_2.4H_2O$ 0.003 g/L, $ZnSO_4.7H_2O$ 0.003 g/L, MOPS 6 g/L, casein hydrolysate 2.5 g/L and $MgHPO_4.3H_2O$ 10 g/L, P-2000 1 ml/L, pH 7.0, autoclaved at about 121 ° C. for about 20 minutes) in a 300 ml Erlenmeyer flask. The flasks were shaken for 3–4 days at about 30° C. Fermentation broth was extracted as described above. *M. rosaria,* ATCC 55709, produced 455 mg/L repromicin under these conditions.

Preparation of 4'-deoxy-O-mycaminosyltylonolide (I) was achieved by feeding repromicin (II) to a fermentation of a strain of the microorganism *Streptomyces fradiae,* ATCC 31733. The strain ATCC 31733 has the property of lacking the genes tyl I and tyl D which are involved in the biosynthetic pathway of tylosin (U.S. Pat. Nos. 4,304,856, 4,419,508, 4,423,148, 4,528,369). *Streptomyces fradiae,* ATCC 31733, was obtained from the ATCC and the method of propagation is standard in the art and can be found in the U.S. patents listed above. The *Streptomyces fradiae,* ATCC 31733, culture can be grown at 24° to 36° C. under submerged conditions with agitation and aeration on media consisting of carbohydrate sources such as sugars, starches, glycerol; organic nitrogen sources such as soybean meal, casamino acids, yeast extract; growth substance such as grain soluble, fish meal, cotton seed meal; mineral salts containing trace elements such as iron, cobalt, copper, zinc, etc.

Inoculum is prepared by scraping vegetative cells from slants inoculated with ATCC 31733 culture. A suitable solid medium for initial growth on slants is ATCC medium 196 (ISP #2, Difco 0770), the components of which are listed below:

| ATCC #196 | Grams/liter |
|---|---|
| Yeast Extract | 4 |
| Malt Extract | 10 |
| Dextrose | 4 |
| Agar | 20 |

The foregoing components are mixed with distilled water to a final volume of 1000 ml and adjusted the pH to 7.2 with KOH.

Inoculum for the preparation of the compound according to this invention may be obtained by employing growth from a slant of the culture or a vial inoculated with the culture. The growth may be used to inoculate either shaker flasks or inoculum tanks or the inoculum tanks may be seeded from the shaker flasks. Growth in shaker flasks will generally have reached its optimum level in 4 to 5 days whereas inoculum in submerged inoculum tanks will usually be in the most favorable period in 2 to 3 days.

Cultivating *Streptomyces fradiae*, ATCC 31733, before and during the biotransformation of repromicin is conducted in a similar manner to that employed in previous fermentations yielding tylosin. Cultivation preferably takes place in aqueous nutrient media under submerged aerobic conditions with agitation at a temperature of 24° to 36° C. Nutrient media useful for cultivation include a source of assimilable carbon such as sugars, starches and glycerol; a source of organic nitrogen such as soybean meal, casamino acids and yeast extracts; a source of growth substances such as grain soluble, fish meal, cotton seed meal; and mineral salts containing trace elements such as iron, cobalt, copper, zinc, etc. Buffering agents such as calcium carbonate and phosphates are used as well. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of sterile free air per volume of fermentation broth per minute forced into the broth through a sparger. Agitation may be maintained by means of agitators generally familiar to those skilled in the fermentation art. The rate of agitation depends on the type of agitator employed. A shaker flask is usually run at 150 to 200 cycles per minute whereas a fermentor is usually run at 300 to 1700 revolutions per minute. Aseptic conditions must, of course, be maintained through the transfer of the organism and throughout its growth.

The culture is usually allowed to grow before repromicin is added to the fermentation medium. Repromicin can be added to the fermentation at the time of inoculation to 96 hours after inoculation, preferably 24 to 48 hours after inoculation. The concentration of repromicin can range from 200 mg/L to 1600 mg/L, preferably 1000 to 1200 mg/L. Repromicin can be dissolved in a number of solvents such as water, methanol, DMSO, etc. The choice of solvent depends on the time of addition and the concentration of repromicin. Biotransformation can also be conducted in the presence of cerulenin which has the effect of inhibiting tylactone formation. After repromicin is added, the fermentation is allowed to continue for a period of time ranging from one to seven days before harvest, preferably 3 to 4 days.

4'-Deoxy-O-mycaminosyltylonolide and a number of macrolides are co-produced in the fermentation broth. The progress of the biotransformation can be monitored by High Performance Liquid Chromatography (HPLC). General HPLC procedures are as follow:

Column: Intersil C8, 5 μm, 4.6×250 mm (available from GL Sciences Inc., Tokyo, Japan);

Mobile Phase: 70% buffer (50mm $KH_2PO_4$, pH 3.5) / 30% acetonitrile;

Flow: 1 ml/minute;

Detection: 282 nm; and

Retention times: 4'-Deoxy-O-mycaminosyltylonolide, 5.5 minutes; repromicin, 42 minutes 4'-Deoxy-O-mycaminosyltylonolide and other macrolides produced by fermentation of *Streptomyces fradiae*, ATCC 31733, may be separated and recovered by conventional methods, e.g., extracting the whole unfiltered fermentation broth with an organic solvent such as chloroform, ethyl acetate, methyl isobutyl ketone or butanol at an elevated pH. Alternatively, the mycelium can be separated after growth has been completed and the mycelium extracted with an organic solvent. The solvent extract can then be concentrated to a thin syrup and the pure compound obtained by chromatography. The whole broth can also be recovered by batch absorption on resin such as XAD-16. The resin is then screened from the fermentation broth. Organic solvent such as acetone is used to elute the product. The organic stream is subsequently concentrated and partially purified using a series of extractions in solvent such as ethyl acetate. The solvent extract can then be concentrated to a thin syrup and the pure compound obtained by chromatography.

Example 1

Fermentation

4'-Deoxy-O-mycaminosyltylonolide was produced by feeding repromicin to a fermentation of a *Streptomyces fradiae*, ATCC 31733. Inoculum was prepared by growing the culture in Fernbach flasks (2.8 liters capacity), the Fernbach flasks were seeded with 0.5 ml to 2 ml of the vegatative culture, containing 500 ml of the following medium:

| Material | Grams/liter |
|---|---|
| Sucrose | 10 |
| Nutrisoy ®[1] | 5 |
| Corn Steep Liquor | 10 |
| Tastone ®[2] | 5 |
| $CaCO_3$ | 3 |
| Soybean Oil | 5 |
| $MgSO_4.7H_2O$ | 1.5 |

[1] Nutrisoy ® is a product of Archer Daniels Midland Co.
[2] Tastone ® is a product of Marcor Corporation.

The medium was adjusted to pH 7.0 with potassium hydroxide and sterilized by autoclaving the flasks at about 121 ° C. for 45 minutes before use. After seeding with the culture, the flasks were incubated for three days at a temperature of about 28° C. on a gyrotary shaker at a speed of 200 rpm. Eight flasks were then composited and used to inoculate the production fermenter, a 200 liter vessel containing 80 liters of the following medium:

| Material | Grams/liter |
|---|---|
| Soybean Oil | 30 |
| Fishmeal | 17.5 |
| Corn Flour | 15 |
| Crude B Molasses | 20 |
| $CaCO_3$ | 2 |
| NaCl | 1 |
| $(NH_4)_2HPO_4$ | 0.4 |

The medium was adjusted to pH 7.2 with sodium hydroxide and sterilized at 121 ° C. for 60 minutes. After cooling, the fermenter was supplied with sterile air at a rate of 40 standard liters per minute and agitated at a speed of 100 rpm. Inoculation was with the flasks described herein above. The fermenter was allowed to run at about 29° C. and the pH was maintained above 6.5 throughout the run. About thirty-six hours after inoculation, an aqueous solution containing 127 grams of repromicin and 20 grams of ammonium chloride was added to the fermenter. About eighty-nine hours after the addition, the fermenter had an apparent assay of 1516 ppm of 4'-deoxy-O-mycaminosyltylonolide according to the HPLC assay described earlier.

Recovery.

After the fermentation broth was transferred to a mixing tank, 10.7 Kgm of XAD-16 were added to the broth. After mixing the resin and broth for two hours, the broth was passed through an 80 mesh screen, and the resin collected. The resin was stirred in 10 gallons of water for about 30 minutes, and filtered over a Nutsche filter with a paper cloth. Acetone (10 gallons) was passed through the filter, and this product containing stream was concentrated to approximately 1 gallon. After adjusting the pH to 3.5, fifteen liters of ethyl acetate was used to extract the product containing concentrate. The 4'-deoxy-O-mycaminosyltylonolide remained in the aqueous layer, and the ethyl acetate layer was decanted. The aqueous layer was then extracted three times with sixteen liters of ethyl acetate at a pH of 9.2. The product containing ethyl acetate layers were then combined and concentrated to 0.72 Kgm of concentrate. Ethyl acetate was then removed in a rotovap apparatus yielding 62.3 grams of brown solid. Fifteen grams of the solid was further purified on a reverse phase HPLC system yielding 4.12 grams of pure 4'-deoxy-O-mycaminosyltylonolide and 0.94 grams of side stream.

What is claimed is:

1. A process for preparing a compound of the formula

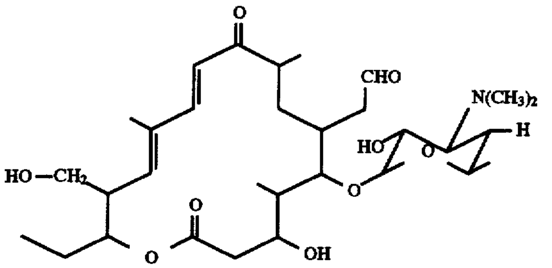

(I)

which comprises fermenting repromicin in an aqueous nutrient medium, under submerged aerobic condition, containing the microorganism *Streptomyces fradiae,* ATCC 31733, wherein the nutrient medium comprises a carbohydrate source, an organic nitrogen source, a growth substance and mineral salts containing trace elements.

2. A process according to claim 1 wherein the compound of formula (I) is isolated.

3. The process according to claim 2 wherein ammonium chloride is added to the aqueous nutrient medium containing the microorganism *Streptomyces fradiae,* ATCC 31733 and repromicin.

4. The process according to claim 3 wherein the fermentation is run for 85 to 95 hours.

* * * * *